United States Patent [19]

MacIntyre

[11] Patent Number: 5,405,831
[45] Date of Patent: Apr. 11, 1995

[54] TREATMENT OF BONE DISORDERS
[75] Inventor: Iain MacIntyre, Heathfield, England
[73] Assignee: Amylin Pharmaceuticals, Inc., San Diego, Calif.
[21] Appl. No.: 98,015
[22] Filed: Jul. 27, 1993

Related U.S. Application Data

[63] Continuation of Ser. No. 964,128, Oct. 20, 1992, abandoned, which is a continuation of Ser. No. 646,644, Feb. 11, 1991, abandoned.

[30] Foreign Application Priority Data

Jul. 8, 1989 [GB] United Kingdom ............... 8915712

[51] Int. Cl.$^6$ ............... A61K 37/02; C07K 7/08
[52] U.S. Cl. ............... 514/4; 514/12; 530/303; 530/307; 530/324
[58] Field of Search ............... 514/12, 4; 530/307, 530/324, 303

[56] References Cited

FOREIGN PATENT DOCUMENTS

| | | |
|---|---|---|
| 0156772 | 2/1985 | European Pat. Off. |
| 0289287 | 2/1988 | European Pat. Off. |
| 0309100 | 3/1989 | European Pat. Off. |
| 0309100 | 3/1989 | European Pat. Off. |
| PCT/US92/-00692 | 1/1992 | WIPO |

OTHER PUBLICATIONS

Cooper et al. PNAS USA vol. 85, 7763 (Oct. 1988).
Taggart, H. M. et al. Lancet, vol. 1, 475 (1982).
Thalassinos et al., Clin. Sci.., 62, 221–226 (1982).
Horsman et al., "The effect of estrogen dose on postmenopausal bone loss," N. Engl. J. Med., 309, 1405–1407 (1983).
Szanto J. and Sandor J., Clinical Trials J., 20, 266 (1983).
Aloia et al., "Risk factors for postmenopausal osteoporosis," Am. J. Med., 78, 95–100 (1985).
Tiegs, R. S. et al. New England Journal of Medicine, 312, 1097 (1985).
MacIntyre I., British Medical Bulletin, 42, 343 (1986).
McEwan, J., et al. Circulation 74,1243–1247 (1986).
Cooper et al., Proceedings of the National Academy of Sciences, U.S.A., 84, 8628 (1987).
Oxford Textbook of Medicine, Eds. Weatherall, Ledingham & Warrell, p. 17.22. (Oxford Medical Publications, 2nd edition, 1987).
Oxford Textbook of Medicine, p. 10.68, supra.
Tippins, J. R., et al., Neuropeptides 4,425–434 (1987).
Breimer, L. H., Zaidi, M., MacIntyre, I, Biochem. J. 255, 377–390 (1988).
Cooper, G. J. S., et al., Proc. Natl. Acad. Sci. 85,7763–7766 (1988).
Leighton, B., Cooper, G. J. S., Nature 335,632–635 (1988).
Zaidi, M., et al. Quart. J. Exp. Physiol. 73,471–485 (1988).
Cooper et al., Biochem. Biophys. Acta, 1014, 247 (1989).
Data H. K., et al. Biochem. Biophys. Res. Commun., 162, 876 (1989).
MacIntyre, I., Lancet, 1989, Oct. 28, 1026.

(List continued on next page.)

Primary Examiner—Lester L. Lee
Attorney, Agent, or Firm—Lyon & Lyon

[57] ABSTRACT

Use of amylin, or variants of amylin, as well as amylin agonists, for the treatment of bone disorders, in particular osteoporosis, Paget's disease, and malignant deposits in bone, bone loss of malignancy or endocrine disorders or autoimmune arthritides or immobility and disuse, and in other conditions where a hypocalcaemic effect is of benefit. Functional peptide fragments of amylin, or a variant of amylin or amylin fragment, are provided as well as a soluble amylin, amylin fragments, or variants thereof, or a lyophilized product, or an oral formulation for use alone, or in combination with other agents, including insulin (or insulin-stimulating agents, including but not limited to the sulfonylureas) and estrogens, for the treatment of disorders of bone or calcium balance.

15 Claims, 1 Drawing Sheet

OTHER PUBLICATIONS

Martindale, *The Extra Pharmacopoeia*, Ed. James E. F. Reynold, p. 1386 (London, The Pharmaceutical Press, 1989).

Martindale, p. 1339, *supra*.

Molecular & Cellular Biology of Diabetes Mellitus vol. III. Alan R. Liss, New York, 1989, p. 123).

Molecular and Cellular Biology of Diabetes Mellitus vol. III, ibid. p. 118.

Prager et. al. *Diabetes*, 1990, vol. 39, p. 116A.

Zaidi et. al., *J. Endocrinol* 126, 473–481 (1990).

Auch, D. et al., "Exon trap cloning: using PCR to rapidly detect and clone exons from genomic DNA fragments", Nucleic Acids Res. 18(22): 6743–7644 (1990).

Khne T., et al., "Evidence against a scanning model of RNA splicing", The EMBO Jour. 2(5): 727–733, (1983).

Wieringa, B., et al., "A Minimal Intron Length but No Specific Internal Sequence is Required for Splicing the Large Rabbit beta–Globin Intron" Cell, 37:915–925, (1984).

Buckler, A. J., et al., "Exon amplification: A strategy to isolate mammalian genes based on RNA splicing", Proc. Natl. Acad. Sci. USA, 88:4005–4009, (1991).

Malim, M. H., et al., "Immunodeficiency virus rev trans-activator modulates the expression of the viral regulatory genes", Nature, 335:281–283, (1988).

Taylor, et al., "The isolation of a cDNA from the Huntington's Disease Candidate region by Exon amplification", Am. J. Hum. Genet. 49(4 Suppl.). (1991).

TREATMENT OF BONE DISORDERS

This application is a continuation of application Ser. No. 07/964,128, filed Oct. 20, 1992, and now abandoned, which is a continuation of application Ser. No. 07/646,644, filed Feb. 11, 1991, now abandoned.

FIELD OF THE INVENTION

The present invention relates to the use of amylin and amylin agonists in the treatment of bone disorders, in particular osteoporosis, Paget's disease, and malignant deposits in the bone, bone loss consequent upon malignancy or endocrine disorders or autoimmune arthritides or immobility and disuse, and other disorders or conditions where a hypocalcaemic effect is of benefit.

BACKGROUND

Disorders of bone metabolism in which there is excessive resorption or remodelling of bone involving an imbalance between osteoclast (bone resorbing cells) and osteoblast (bone depositing cells) activity are widespread and include osteoporosis, Paget's disease of bone, and familial idiopathic hyperphosphatasemia. Bony metastases from malignant tumors are also a common feature of most forms of cancer and give rise to serious problems including severe pain, fractures, and hypercalcaemia.

Osteoporosis is a disorder of the skeleton associated with the loss of both hydroxyapatite (calcium phosphate complexes) and protein matrix (colloid). The result is thinning and weakening of the bones and an increased incidence of fractures, particularly compression fractures of the vertebrae and fractures of the hip and wrist from minimal trauma. In older patients it is called "senile osteoporosis" and affects both sexes. Coming after menopause it is referred to as "postmenopausal osteoporosis" and occurs in about one third of such women. Unfortunately, substantial bone loss must occur before it can be detected with routine radiographic procedures. There are a variety of current therapies for these disorders, none of which is accepted as adequately effective, and some of which have markedly adverse side effects. Hormonal therapies sometimes used for osteoporosis include androgens, estrogens, and calcitonin.

Many different methods of treatment have been tried with the aim of increasing bone density and substance. After several months of estrogen replacement in postmenopausal patients, for example, calcium balance becomes positive and bone resorption can decrease to normal. Thalassinos et al., Clin. Sci., 62, 221-226 (1982). The effects of estrogens in preventing postmenopausal bone loss are dose related. While the equivalent of 15 $\mu$g of ethinyl estradiol daily can prevent vasomotor symptoms in menopause, doses of 15 to 25 $\mu$g daily are required to prevent bone loss and 25 $\mu$g or more per day can result in a net increase in bone density (Horsman et al., "The effect of estrogen dose on postmenopausal bone loss," N. Engl. J. Med., 309, 1405-1407 (1983). The positive effects of estrogen on calcium balance and bone density are reversed rapidly when treatment is discontinued Aloia et al., . "Risk factors for postmenopausal osteoporosis," Am. J Med , 78, 95-100 (1985). Chronic estrogen replacement therapy is increasingly recommended for postmenopausal women and can reduce the incidence of osteoporotic fractures. While earlier concerns over increased incidence of breast cancer are now reduced, there is a well documented increased risk of endometrial hyperplasia and uterine cancer. Martindale, The Extra Pharmacopoeia, Ed. James E. F. Reynold, page 1386 (London, The Pharmaceutical Press, 1989). Since most cases of osteoporosis occur in females, masculinizing side effects as well as adverse effects on liver function make the androgens an undesirable form of therapy. Injections, or nasal sprays, of salmon calcitonin or Elcatonin, a synthetic variant of eel calcitonin, are widely used in some countries in patients with osteoporosis, although clinical data supporting the utility is not universally accepted. See, e.g., Taggart, H. M. et al. Lancet, 1, 475 (1982); Tiegs, R. D. et al. New England Journal of Medicine, 312, 1097 (1985). One aspect of post-menopausal senile osteoporosis that may respond to calcitonin treatment is bone pain. Problems with calcitonin therapy, aside from the question of efficacy, include nausea, tingling, flushing, gastrointestinal disturbance, and disturbance of taste. Martindale, page 1339, supra. Also, formation of antibodies occurs. Other treatments for osteoporosis, including, calcium supplements, Vitamin D, and disphosphonates are sometimes used. However, thus far, their efficacy in established osteoporosis is not convincingly established. Salmon calcitonin is currently the medical treatment of choice in Paget's disease. Oxford Textbook of Medicine, Eds. Weatherall, Ledingham & Warrell, page 17.22. (Oxford Medical Publications, 2nd edition, 1987). Also, salmon calcitonin has shown benefit in bone metastasis, (Szanto J. and Sandor J., Clinical Trials J., 20, 266 (1983), though whether this is an action on bone or on the central nervous system is not yet certain. MacIntyre I., British Medical Bulletin, 42, 343 (1986). For hypercalcemic episodes from a variety of causes, intravenous or intramuscular injections of calcitonin can be an effective treatment, though the effect may be relatively short acting, Oxford Textbook of Medicine, page 10.68, supra, perhaps because of receptor down-regulation.

Thus, it will be appreciated that in each of these disorders of bone and calcium metabolism the existing therapies can have serious drawbacks in terms of efficacy and/or side effects.

British Patent Application 8709871, filed 27 Apr. 1987, described a novel peptide with the sequence:

```
1                    5                   10
Lys—Cys—Asn—Thr—Ala—Thr—Cys—Ala—Thr—Gln—
11                   15                  20
Arg—Leu—Ala—Asn—Phe—Leu—Val—His—Ser—Ser—
21                   25                  30
Asn—Asn—Phe—Gly—Ala—Ile—Leu—Ser—Ser—Thr—
31                   35
Asn—Val—Gly—Ser—Asn—Thr—Tyr
```

The native molecule contains a disulfide bridge between the cysteine residues shown at positions 2 and 7 in the primary structure, is amidated at the 3' end, and is formed as a propeptide. Both of these post-translational modifications are required for full biologic activity. This peptide, now named amylin, was first isolated in the amyloid deposits in the pancreases of patients with Type 2 diabetes. Cooper et al., Proceedings of the National Academy of Sciences, U.S.A., 84, 8628 (1987). This peptide was discovered to have novel biological effects including enhancement of hepatic glucose output, increased production of lactate from skeletal muscle, and reduced action of insulin in skeletal muscle. See, e.g., Cooper et al., Biochem. Biophys. Acta, 1014, 247 (1989). Amylin is secreted from the beta cells of the islets of Langerhans in the pancreas in response to stimulation by glucose and amino acids, i.e., two food substrates. Amylin is said to be a partner anabolic hormone with insulin, among whose roles is the storage and disposal of food as carbohydrate and fat. Structurally and at the gene level, amylin has the characteristics of a peptide hormone, Cooper et al., ibid, and has homology to the neurotransmitter, calcitonin gene related peptide (CGRP), and to the hormone calcitonin. Cooper et al., ibid; Datta H. K., et al. Biochem. Biophys. Res. Commun., 162, 876 (1989).

This invention arises from the determination that, in addition to some structural homologies, amylin shares certain biological effects with calcitonin and has action on osteoclasts and other aspects of bone and calcium metabolism useful in the treatment of bone disorders and hypercalcaemia. MacIntyre, I., Lancet, 1989, Oct. 28, 1026. A linkage between amylin and bone and calcium metabolism had not been previously suggested, and the linkage between a pancreatic hormone responsive to food substrates and the regulation of bone resorption by osteoclasts was unexpected, as was the fact that amylin can be used for the control of plasma calcium.

SUMMARY OF THE INVENTION

The invention comprises the use of amylin, or variants of amylin, as well as amylin agonists, for the treatment of bone disorders, in particular osteoporosis, Paget's disease, and malignant deposits in bone, bone loss of malignancy or endocrine disorders or autoimmune arthritides or immobility and disuse, and in other conditions where a hypocalcaemic effect is of benefit. Amylin, or a functional peptide fragment of amylin, or a variant of amylin or amylin fragment, is provided as well as a soluble amylin, amylin fragment, or variant thereof, or a lyophilized product, or an oral formulation for use alone, or in combination with other agents, including insulin (or insulin-stimulating agents, including but not limited to the sulfonylureas) and estrogens, for the treatment of disorders of bone or calcium balance. Methods of preparation thereof are provided.

Detailed Description of the Invention

While the specification concludes with claims particulary pointing out and distinctly claiming the subject matter regarded as forming the present invention, it is believed that the invention may be better understood from the following description taken in connection with the accompanying drawings in which:

Figure 1:
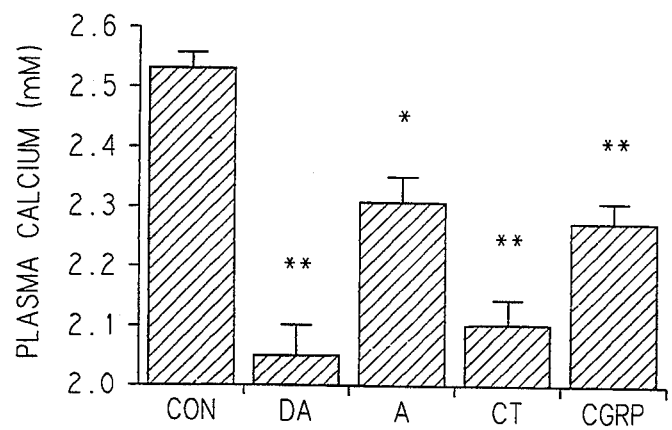
FIG. 1 shows the effect of intravenous injection of 500 pmol deamidated amylin (DA)(Peninsula), amylin (A), asu$^{1-7}$-eel calcitonin (CT)(ISF) or human calcitonin gene-related peptide$\alpha$(CGRP) (Sandoz) or vehicle on plasma calcium levels in 50 g male Wistar rats (n=6 per group).

Amylin is a newly discovered 37 amino acid polypeptide which was isolated and purified by Cooper et al. (1988) supra from amyloid deposits in pancreatic islets obtained from type II diabetics. It has been reported that the amylin gene is located on chromosome 12 and may share a common ancestral gene with the genes for the calcitonin peptide family. The amino acid sequence of amylin also shows structural homology with calcitonin generelated peptide (CGRP), an alternative splice product of the $\alpha$-calcitonin gene, and with calcitonin. It has been shown that CGRP behaves as a weak agonist of calcitonin; it inhibits osteoclastic bone resorption (Zaidi, M., et al. Quart. J. Exp. Physiol. 73, 471–485 (1988) and lowers plasma calcium at a 100 to 100-fold higher molar concentration than does calcitonin. It has been suggested that amylin, previously termed diabetesassociated peptide, is linked to the development of type 2 diabetes. Leighton, B., Cooper, G. J. S. (1988) Nature 335, 632–635 (1988); Cooper, et al. Proc. Natl. Acad. Sci. 85, 7763–7766 (1988). The effect of this polypeptide on carbohydrate metabolism and its role in the development of insulin-resistance has therefore become a focus of intensive investigation.

The effects of amylin and deamidated amylin on calcium metabolism in the rat and rabbit were investigated by two different methods. First, in vivo hypocalcaemic activity was assessed by measuring plasma calcium levels after injection of the peptide in 50 g rats. Next, in vitro resorption of cortical bone by disaggregated rat osteoclasts was quantified by scanning electron microscopy together with image analysis. It was demonstrated that amylin and deamidated amylin have calcitoninlike effects. Both are inhibitors of osteoclastic resorption and lower plasma calcium in both rats and rabbits. Described below are experiments which show the biological activity of both amylin and deamidated amylin using the in vivo rat hypocalcaemia assay and an in vitro bone resorption system. In addition, the effect on plasma calcium levels of infusion of high doses of amylin into rabbits is described.

It has now been demonstrated that both amylin and deamidated amylin have hypocalcaemic effects in the rat and the rabbit. Both peptides also inhibit bone resorption by disaggregated rat osteoclasts. It seems most likely that amylin interacts with the calcitonin receptor. The responses observed with amylin and deamidated amylin were less than for calcitonin, but significantly greater than those observed with CGRP. In decreased order of hypocalcaemic and anti-resorptive activity the peptides can be placed as follows: asu$^{(1-7)}$-eel CT>human CT>amylin/amylin amide>CGRP. Both CGRP and calcitonin require the presence of a C-terminal amide for in vivo biological activity (Breimer, L. H., Zaidi, M., MacIntyre, I, Biochem. J. 255, 377–390 (1988)), but amylin does not require amidation for its in vivo or in vitro actions on bone. The deamidated peptide is also active in significantly reducing glucose incorporation into skeletal muscle glycogen. Leighton, B., Cooper, G. J. S., Nature 335, 632–635 (1988); Cooper, G. J. S., et al., Proc. Natl. Acad. Sci. 85, 7763–7766 (1988). Deamidated amylin failed to stimulate the CGRP-responsive adenylate cyclase of umbilical endothelium. McEwan, J., et al. Circulation 74, 1243–1247 (1986). The infusion experiment in the rabbit shows that amylin exhibits a hypocalcaemic effect, presumably due to an action on osteoclast calcitonin receptors. CGRP is hypocalcaemic at lower doses in rabbits, but at higher doses, also exhibits a parathyroid hormone-like hypercalcemic effect in the rabbit and chick. Tippins, J. R., et al., Neuropeptides 4, 425–434 (1987).

The action of the amylin, calicitonin, and CGRP peptides are mediated by differing potencies and efficacies of interaction with at least three receptors: the osteoclast calcitonin receptor, the vascular CGRP receptor; and the amylin receptor in muscle. Although amylin plays a key role in carbohydrate metabolism in health and diabetes, an influence of amylin in calcium and bone metabolism is now established.

In view of the foregoing, the present invention provides the use of amylin and amylin agonists in the treatment of diseases in which an inhibitory effect on osteoclast activity and/or a hypocalcaemic effect is of benefit. In particular such diseases include for example, osteoporosis, and Pagets disease. Since amylin is co-secreted with insulin and certain physiologic and pathologic conditions (e,g,, fasting, Type 1 diabetes) may cause reduced plasma levels of both hormones, it should in certain circumstances be more effective to administer both insulin (or insulin-stimulating agents) and amylin to gain superior therapeutic results; moreover, since amylin is demonstrated to be able to cause insulin resistance (Cooper et al. 1989 supra) administration of insulin with amylin is expected to reduce any risk of inducing a diabetic or prediabetic state. Furthermore, in view of insulin's known protein-sparing and anabolic actions, the combination of insulin and amylin should be particularly efficacious in restoring organic and mineral components of bone tissue in the disorders described above. From the ratio of insulin to amylin in the pancreas, and in plasma, the dosages of insulin and amylin are expected to be in ranges from about 1:10 to about 100:1.

According to the preferred aspect of this invention, a composition for use in treatment of bone or calcium disorders comprises amylin or a functional fragment or variant (see European Patent Application No. 88303803.6, Publication No. 0 289 287; European Patent Application No. 88307927.9, Publication No. 0 309 100) which is administered by injection, intra-nasally, or in an oral formulation which constitutes an art-known form for enhancing oral bioavailability of peptides or peptide-derived structures. Products according to the invention may be produced in the form of solutions for parental or nasal administrations or as capsules or suspensions for oral administration. In some cases it may be convenient to provide amylin, amylin fragments, or variants, in a single or a combination preparation, together with other agents, including but not limited to those described above which are partially effective therapies in bone and calcium disorders. The dosage is expected to be in the range 0.01 mg to 100 mg per day and a suitable regime will be determined by a doctor for each patient on the basis of: symptomatic relief, e,g., pain; biochemical indicators, e.g. plasma calcium, or x-ray or other measure of bone density and modelling. Also, monitoring of plasma amylin by radio-immunoassay or other sensitive assay will be an adjunct to therapy and the monitoring of diseases associated with hypoamylinemia.

The preparation of amylin, amylin fragments or variants may be by art-known methods of polypeptide chemical synthesis (as in Datta et al. supra) or by recombinant fermentation technology e.g. in *E. coli*, yeast, baculovirus expression vector, or chinese hamster ovaries cells, by art-known methods including combinations of recombinant fermentation and chemical or enzymic modification.

While this invention is concerned with the matters described and claimed herein, the following additional points of explanation and background are of interest. Type 1 diabetes, in which amylin as well as insulin is deficient (e.g. Prager et. al. Diabetes, 1990, 39, page 116A), is associated with "osteopenia" (MacIntyre I., Lancet, 1989, supra; Molecular & Cellular Biology of Diabetes Mellitus Vol. III. Alan R. Liss, New York, 1989, page 123). Moreover, bone loss in postmenopausal Type 2 diabetic women occurred at only approximately half the rate of that seen in controls (Molecular and Cellular Biology of Diabetes, Vol. III, ibid. page 118) and amylin excess is conceived to be a major component of the etiopathology of Type 2 diabetes (Cooper et. al. 1989 ibid). Thus, in conditions in which there is amylin deficiency or amylin excess there is an association with osteoporosis or with protection from osteoporosis respectively lending support by correlation to the underlying concept of this invention.

Figure 2:
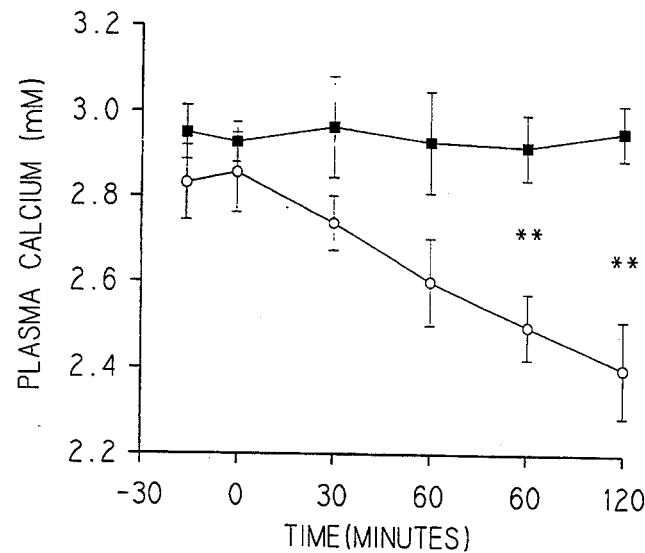
FIG. 2 shows the effect of a continuous infusion into adult rabbits of amylin (Bachem) (500 pmol min$^{-1}$) (open circles) (n=5) or vehicle (closed squares) (n=4) on plasma calcium levels (Statistics by Student's t-test, ** $p<0.01$).

Amylin infusion into young wistar rats or adult rabbits reduced plasma calcium levels from 2.5 nM to 2.05 nM and 2.8 to 2.4 nM respectively (Datta et. al. 1989 supra), see FIGS. 1 and 2. Amylin also reduced the osteoclastic resorption of bone in a dose-dependent fashion, in a system in which rat osteoclasts were isolated and deposited on slices of human cortical bone (Datta et. al. 1989 ibid), see FIG. 3. Furthermore, 1 hour of intravenous infusion of 150 pmol/Kg/min amylin into four human patients with Paget's disease reduced plasma calcium by amounts ranging from 0.05 to 0.37 nM.

A difference between the cellular actions of amylin and calcitonin has been recently revealed by examining the intracellular second messenger pathways and detailed functional responses of isolated osteoclasts. Amylin inhibited osteoclast motility as did calcitonin; however while calcitonin also elevated cytosolic calcium and caused cell retraction, amylin evoked neither of these responses (MacIntyre and Zaidi, unpublished results). Thus, it appears that osteoclast activity may be restrained via two receptor types; calcitonin acts at both while amylin acts mainly via only one, reducing motility, reducing resorption and probably acting via the second messenger cAMP (Zaidi et. al. 1990, J. Endocrinol 126, 473–481.

While amylin is somewhat less potent by 10–30 fold (i,e.,, is active at higher concentrations) than human calcitonin in studies on rat osteoclasts, it was comparably potent to human calcitonin in the studies on human patients with Paget's disease. The different profile of action of amylin and calcitonin on osteoclasts, and amylin's anabolic actions in other tissues, provide a favorable profile for amylin compared with calcitonin in treating the various bone disorders outlined above, particularly in thin, elderly subjects predicted to be deficient in amylin, since amylin is stimulated by food substrates and such subjects often have poor or meager diets, and because amylin excess is associated with obesity. Prager et al. 1990, supra.

EXAMPLE 1

Synthesis and purification of amylin: Solid phase synthesis of amylin was carried out in an Applied Biosystems Inc. (Model 430A) peptide synthesizer using t-butoxcarbonyl (BOC) chemistry. Synthesis was carried out on a 0.5 mmol scale using 4-fold molar excess preformed symmetrical anhydrides of protected amino acids. Each arginine, glutamine and asparagine residue was double coupled in N-dimethylformamide. The BOC group gave protection for all amino acids. All side chain protection groups were sensitive to trifluoromethanesulfonic acid (TFMSA) (for example mesitylene-2-sulphone for arginine, Mob for cysteine, benzyl ether for aspartic acid, glutamic acid benzyl ether for serine and threonine and Tos for histidine). On the completion of the synthesis, the protected peptide resin was cleared with TFMSA and purified by reverse-phase high performance liquid chromatography. The amino acid sequence of the synthetic material amylin was confirmed by gas phase sequencing.

EXAMPLE 2

Animal experiments: Fifty gram male Wistar rats (mean weight±SEM, 51±1.2 g, Charles Rivers, Margate, Kent) were fasted overnight with ad lib access to water and used for experiments. Groups of rats (n=6 per group) were injected with vehicle or 500 pmol each of amylin, deamidated amylin (Bachem Pharmaceuticals, Ltd), $asu^{1-7}$-eel calcitonin (CT), or human calcitonin gene-related peptide-$\alpha$ (CGRP). Following injection the animals were bled into heparinized syringes. Rabbits were infused with saline or amylin (500 pmol $min^{-1}$) for 90 minutes via a 21 G needle inserted into the lateral ear vein. The needle was connected to a pump via a polythene cannula (Portex, 00, Hythe, Kent). Blood samples were taken at timed intervals before and after the infusion was commenced. Plasma was separated and calcium levels measured by DC Plasma Emission Spectrophotometry.

Effects on plasma calcium: Both amylin and deamidated amylin produced a marked hypocalcaemia in 50 g rats after intravenous injection. The results, shown in FIG. 1, indicate that the response was similar to that produced by calcitonin and CGRP although relative potencies could not be deduced from their near-maximum effects. As shown by FIG. 2, the infusion of amylin into rabbits at a dose of 500 pmol per minute over 90 minutes caused a marked lowering of plasma calcium and a trend was apparent within 30 minutes. The calcium levels continued to fall for 30 minutes after the end of the infusion (FIG. 2).

EXAMPLE 3

Figure 3:
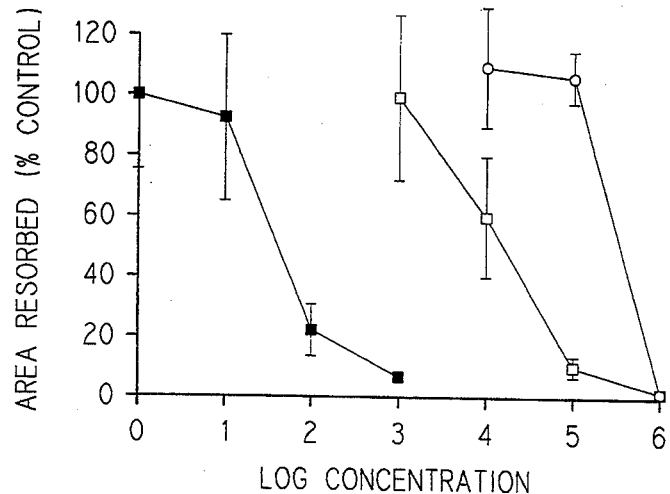
FIG. 3 shows the Log$_{10}$ dose-response curves showing the effect of deamidated amylin (Peninsula) (open squares), asu$^{1-7}$-eel calcitonin (closed squares) (ISF) or human calcitonin gene-related peptide-$\alpha$ (Sandoz) (open circles) (ng1$^{-1}$) on the total area of osteoclastic resorption per bone slice (expressed as a percentage of control resorption).

Bone resorption assay: Human cortical bone slices were prepared as previously described (Zaidi et al. Quart. J. Exp. Physiol. 73, p. 471 (1988). The slices were then cut into pieces, each measuring about 3 $mm^2$. Newborn Wistar rats were killed by decapitation and their femora and tibiae removed. The bones were freed of adherent soft tissues and cut across their epiphyses in Medium 199 with foetal calf serum (FCS, 10%, v/v) and antibiotics (Flow Laboratories, UK, Ltd.). Osteoclasts were placed in suspension and allowed to settle for 10 seconds, before the supernatant was dropped onto 30 to 35 bone slices placed in a well of a Sterilin 100 18 mm multiwell dish. Following incubation (37° C.; 15 minutes), the bone slices were removed, washed gently in Minimal Essential Medium with FCS (10%, v/v) (MEM/FCS) and placed in separate wells (each well contained 5-6 slices and 900 $\mu$l MEM/FCS). Either one or two homogeneous suspensions of osteoclasts were used for each experiment. When two suspensions were used, the experiment was divided into two blocks, each of which included all treatments and one suspension. After further incubation (37° C., 10% humidified $CO_2$, 10 minutes), 100 $\mu$l of MEM/FCS containing the test substance was added. Finally, bone slices were incubated overnight (37° C., 10% humidified $CO_2$, 18 hours) and quantified in terms of cell numbers and bone resorption. After fixation in glutaraldehyde, cells were stained with toluidine blue and examined by transmitted light microscopy. In order to rule out toxic effects, osteoclasts were counted on three slices for every variable and their numbers were then compared on hormone-treated and control bone slices. The slices were bleached by immersion in sodium hypochlorite solution (10% v/v) for 30 minutes and dehydrated in aqueous ethanol (80% v/v). The slices were then sputter coated with gold, randomized and examined in a Cambridge 360 Scanning Electron Microscope (Cambridge Instruments, Cambridgeshire). Osteoclastic excavations, each defined by a continuous border within an area of unresorbed bone were counted. The area of bone surface resorbed was calculated by tracing the outline of the concavities into an image processor (Sight Systems, Newbury, Berks). Amylin and deamidated amylin caused a marked reduction of the total area of bone resorbed by isolated osteoclasts, without affecting cell number of viability, as shown by FIG. 3. The effects were concentration-dependent and similar to those produced by calcitonin and CGRP, but since the peptides were not all compared in the same assay, precise potency ratios are not available. However, amylin and deamidated amylin did not differ significantly. Both are less potent than human calcitonin by about an order of magnitude (MacIntyre, Lancet 1989, supra), but more potent than CGRP.

I claim:

1. A method for the treatment of a subject suffering from a bone disorder associated with excessive resorption or remodeling of bone tissue comprising administering to said subject a therapeutically effective amount of amylin in association with a pharmaceutically acceptable carrier.

2. A method according to claim 1 wherein said bone disorder is selected form the group consisting of osteoporosis; Paget's disease; and bone loss resulting from malignancy, an endocrine disorder, autoimmune arthritides, breakage and fracture, or immobility and disuse.

3. A method according to claim 1 or 2 further comprising administering insulin.

4. A method for the treatment of a subject suffering from a bone disorder associated with excessive resorption or remodeling of bone tissue comprising administering to said subject a therapeutically effective amount of an amylin agonist effective to reduce said subject's blood calcium level and/or effective to reduce bone resorption in association with a pharmaceutically acceptable carrier, wherein said amylin agonist is not a CGRP or a calcitonin.

5. A method according to claim 4 wherein said bone disorder is selected form the group consisting of osteoporosis; Paget's disease; and bone loss resulting from malignancy, an endocrine disorder, autoimmune arthritides, breakage and fracture, or immobility and disuse.

6. A method according to claim 4 or 5 further comprising administering insulin.

7. A method for the treatment of a subject suffering from hypercalcaemia, comprising administering to said subject a therapeutically effective amount of amylin in association with a pharmaceutically effective carrier.

8. A method for the treatment of a subject suffering from hypercalcaemia, comprising administering to said subject a therapeutically effective amount of an amylin agonist effective to reduce said subject's blood calcium level, in association with a pharmaceutically effective carrier, wherein said amylin agonist is not a CGRP or a calcitonin.

9. A method for the treatment of a subject suffering from a bone disorder associated with hypoamylinemia, comprising administering to said subject a therapeutically effective amount of amylin in association with a pharmaceutically acceptable carrier.

10. A method for the treatment of a subject suffering from a bone disorder associated with hypoamylinemia, comprising administering to said subject a therapeutically effective amount of an amylin agonist in association with a pharmaceutically acceptable carrier, wherein said amylin agonist is not a CGRP or a calcitonin.

11. A method for the treatment of a subject suffering from a bone disorder associated with excessive resorption or remodeling of bone tissue comprising administering to said subject a therapeutically effective amount of deamidated amylin in association with a pharmaceutically acceptable carrier.

12. A method according to claim 11 wherein said bone disorder is selected form the group consisting of osteoporosis; Paget's disease; and bone loss resulting from malignancy, an endocrine disorder, autoimmune arthritides, breakage and fracture, or immobility and disuse.

13. A method according to claim 11 or 12 further comprising administering insulin.

14. A method for the treatment of a subject suffering from hypercalcaemia, comprising administering to said subject a therapeutically effective amount of deamidated amylin in association with a pharmaceutically effective carrier.

15. A method for the treatment of a subject suffering from a bone disorder associated with hypoamylinemia, comprising administering to said subject a therapeutically effective amount of deamidated amylin in association with a pharmaceutically acceptable carrier.

* * * * *